US00PP29634P3

(12) United States Plant Patent
Wirthensohn et al.

(10) Patent No.: US PP29,634 P3
(45) Date of Patent: Sep. 4, 2018

(54) ALMOND VARIETY NAMED 'RHEA'

(50) Latin Name: *Prunus dulcis*
Varietal Denomination: RHEA

(71) Applicants: ADELAIDE RESEARCH & INNOVATION PTY LTD, Adelaide (AU); HORTICULTURE INNOVATION AUSTRALIA LIMITED, Sydney (AU)

(72) Inventors: Michelle Wirthensohn, Adelaide (AU); Andrew Granger, Montacute (AU)

(73) Assignees: Adelaide Research & Innovation Pty Ltd, Adelaide (AU); HORTICULTURE INNOVATION AUSTRALIA LIMITED, Sydney (AU)

( * ) Notice: Subject to any disclaimer, the term of this patent is extended or adjusted under 35 U.S.C. 154(b) by 0 days.

(21) Appl. No.: 14/999,563

(22) Filed: May 26, 2016

(65) Prior Publication Data

US 2017/0347508 P1 Nov. 30, 2017

(51) Int. Cl.
*A01H 5/08* (2006.01)

(52) U.S. Cl.
USPC ..... Plt./155
CPC ..... *A01H 5/0837* (2013.01)

(58) Field of Classification Search
USPC ..... Plt./155
CPC ..... A01H 5/0825; A01H 5/0837
See application file for complete search history.

*Primary Examiner* — Kent L Bell
(74) *Attorney, Agent, or Firm* — Marshall, Gerstein & Borun LLP

(57) ABSTRACT

A new and distinct almond variety of *Prunus dulcis* named 'RHEA', particularly characterized by attractive medium sized kernels and very high production. Other desirable characteristics include medium harvest time, well-sealed paper shells, with kernels having high oleic acid content.

3 Drawing Sheets

Latin name of the genus and species of the plant claimed: *Prunus dulcis*.

Variety denomination: 'RHEA'.

BACKGROUND OF THE INVENTION

The present invention relates to a new and distinct cultivar of almond varieties, botanically known as *Prunus dulcis*, and hereinafter referred to by the name 'RHEA'.

The disclosure provides a new and distinct variety of almond tree, botanically known as *Prunus dulcis*, synonymous with *Prunus amygdalus* Batsch., *Amygdalus communis* L., and *Amygdalus dulcis* Mill., which belongs to the Rosaceae family, and is hereinafter referred to by the variety denomination 'RHEA'.

The new *Prunus dulcis* variety is a product of a controlled breeding program conducted by the inventors Michelle Wirthensohn and Andrew Granger in Adelaide, Australia. The objective of the breeding program was to develop new almond varieties with high production, self-fertility and good kernel characteristics.

The new *Prunus dulcis* 'RHEA' originated from a cross in 1998 in Adelaide, Australia. The female or seed parent is *Prunus dulcis* variety designated 'Le Grand' (unpatented) and the male or pollen parent is an Australian *Prunus dulcis* variety designated 'Keane' (unpatented). The new *Prunus dulcis* 'RHEA' was selected by the inventors from the progeny of the stated cross in field trials in 2009 in Lindsay Point, Australia. First observations occurred in 2005.

Asexual propagation of the new *Prunus dulcis* 'RHEA' by grafting onto *Prunus persica* (L.) Batsch rootstock designated 'Nemaguard' (unpatented) was first performed in 2005 in the orchard located in Lindsay Point, Australia. Asexual propagation of the new *Prunus dulcis* 'RHEA' has confirmed that the characteristics as herein disclosed for the new variety are stable and retained through successive generations of asexual propagation. The new variety propagates true-to-type.

Asexual reproduction of the new almond tree has shown that the unique features of this new almond tree are stable and reproduced true to type in successive generations of asexual reproduction.

SUMMARY OF THE INVENTION

The 'RHEA' variety of almond is of medium to large size, medium to strong vigor with slightly open growth and demonstrates very high and regular production of paper shell nuts with kernels having an excellent flavour with a light semibitter taste. The harvest maturity is slightly later than 'Nonpareil' (unpatented). Doubles are not produced under growing conditions in the Riverland area of South Australia. The tree is self-incompatible but cross-compatible with 'Nonpareil' (unpatented), 'Peerless' (unpatented), 'Sonora' (unpatented) and 'Monterey' (unpatented).

The following traits have been repeatedly observed and are determined to be the unique characteristics which make the new variety 'RHEA' clearly distinguishable from its parents and the variety most similar of common knowledge which is 'Somerton' (unpatented):

1. very high productivity;
2. well-sealed paper shells; and
3. predominantly spur-bearing.

The following characteristics listed in Table 1 have been repeatedly observed in combination and distinguish 'RHEA' as a new and distinct almond variety:

TABLE 1

| Trait | New variety 'RHEA' | Female parent 'Le Grand' (unpatented) | Male parent 'Keane' (unpatented) | Most similar variety of common knowledge 'Somerton' (unpatented) |
|---|---|---|---|---|
| Shell type | Paper | Semihard | Soft | Soft |
| Tree habit | Slightly open | Upright | Upright | Open |
| Self-fertility | Absent | Present | Absent | Absent |
| Flowering time | Early | Medium | Early | Early |
| Kernel size | Medium | Medium | Large | Medium |
| Time of maturity | Medium | Early to medium | Early-medium | Early to medium |

Distinguishing characteristics of 'RHEA' are set out in Table 1. Plants of the new 'RHEA' almond tree have not been observed under all possible environmental conditions and cultural practices. The phenotype may vary somewhat with variations in environment, such as temperature, day length and light intensity, without, however, any variance in genotype.

The primary difference between the new variety and the female parent 'Le Grand' (unpatented) is the new variety is self-sterile, whereas 'Le Grand' (unpatented) is self-fertile and does not require a pollinator tree planted near to fertilize the flowers and, thus, produce almonds. In comparison to its male parent 'Keane' (unpatented), the new variety has slightly open growth habit, whereas 'Keane' (unpatented) has upright growth habit.

The primary difference between the new variety and the most similar variety of common knowledge 'Somerton' (unpatented) is the new variety has ovate shaped dry fruit with light colored kernels, whereas 'Somerton' (unpatented) has elliptic shaped dry fruit with dark colored kernels.

BRIEF DESCRIPTION OF THE DRAWING

The accompanying photographs (drawings) illustrate the overall appearance of the new *Prunus dulcis* 'RHEA' showing the colors, as true as is reasonably possible with digital reproduction. Colors in the photographs may differ slightly from the color values cited in the detailed botanical description, which accurately describe the color of 'RHEA'. The trees were grown on Nemaguard rootstock.

DETAILED BOTANICAL DESCRIPTION

Figure 1:
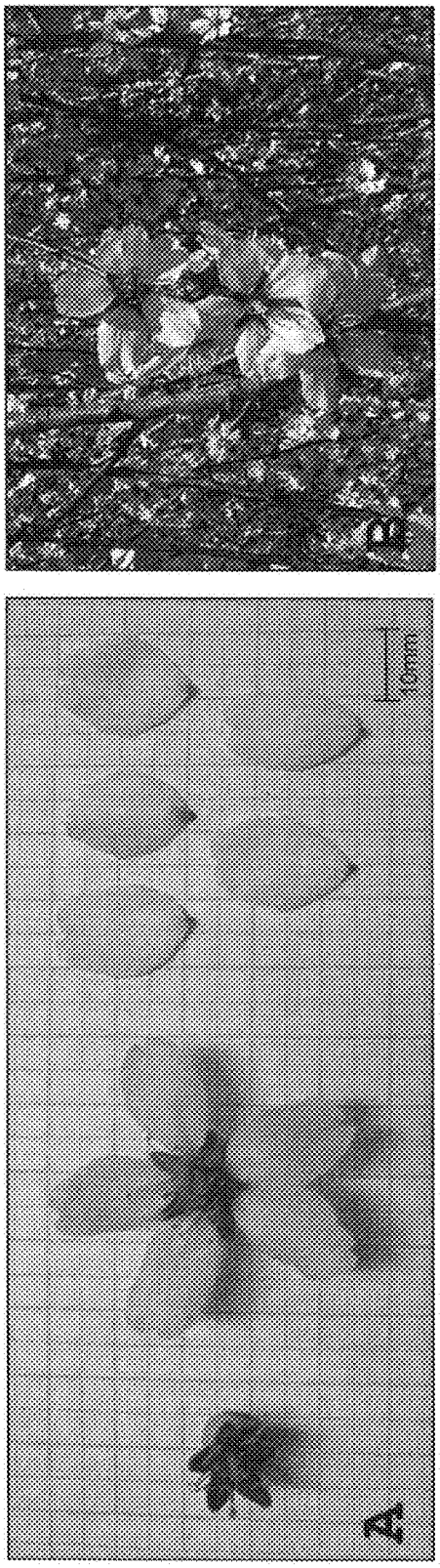
FIG. 1 shows typical flowers of 'RHEA', dissected (FIG. 1A) and in situ (FIG. 1B).
Figure 2:
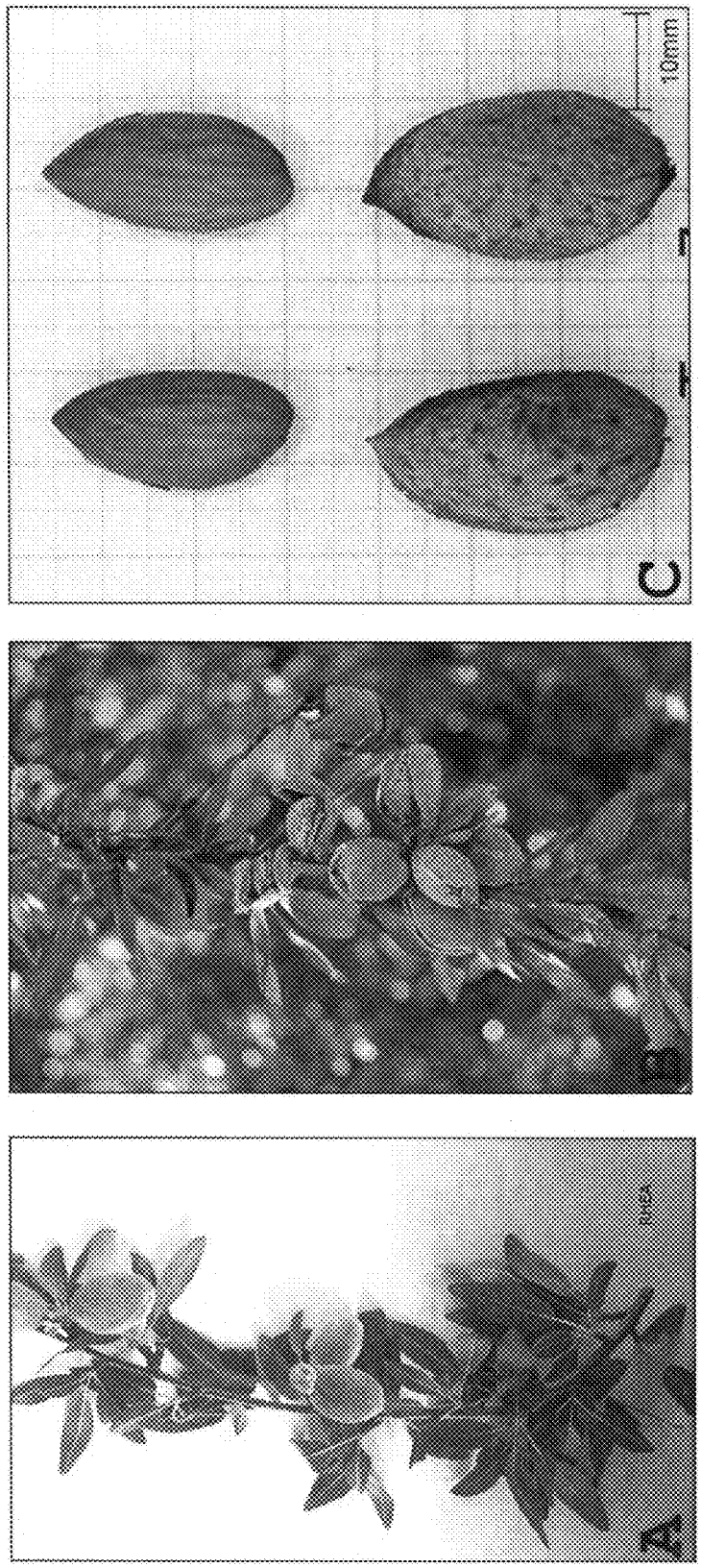
FIG. 2 shows various images of fruit of 'RHEA', including a one year-old shoot, showing green immature fruit (FIG. 2A), mature fruit in situ (FIG. 2B), and kernel and dry fruit shape (FIG. 2C).
Figure 3:
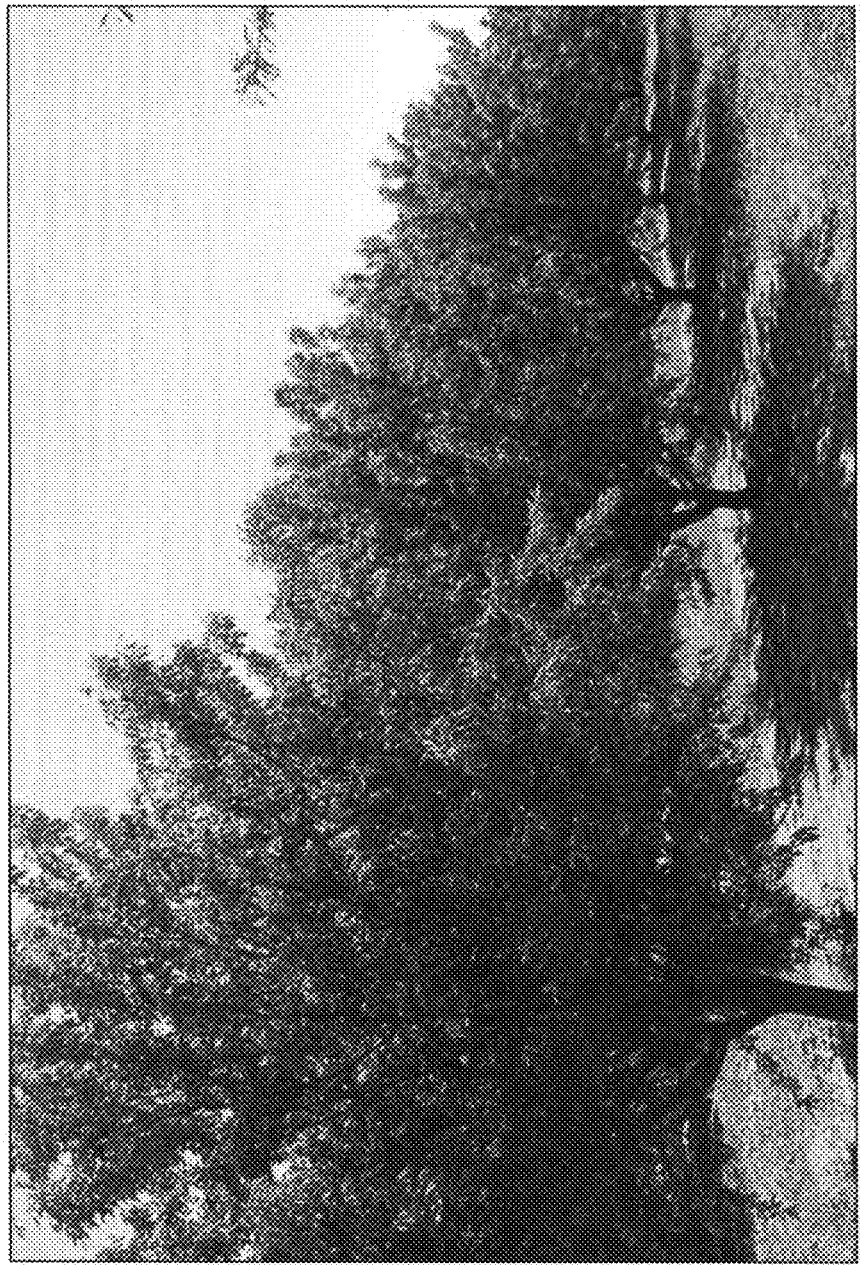
FIG. 3 shows a typical four year-old tree of 'RHEA' on 15 Sep. 2010.

Plants used in the aforementioned photographs and in the following description were grown outside under natural season conditions and cultural practices which approximate those generally used in commercial almond production. During the production of the plants, day temperatures ranged from about 14.5° C. to 48.2° C., night ranged from about −5.7° C. to 14° C. and light levels ranged from about 126,905 to 564,729 foot-candles. Measurements and numerical values represent averages for typical flowering plants.

The following is a detailed description of the new 'RHEA' variety when observed during the growing seasons from 2010 to 2015 at Lindsay Point, Victoria, Australia. During 2015, the 'RHEA' trees were nine years of age. Quantified measurements are expressed as an average of measurements taken from a number of trees of 'RHEA'. The measurements of any individual tree (or any group of trees) of 'RHEA' may vary from the stated average.

Color references are made to The Royal Horticultural Society Colour Chart (R.H.S.)., sixth edition, (2015). Color values were taken under conditions of natural light.

All of the trees of 'RHEA', insofar as they have been observed, have been consistent in the characteristics described below.

Classification:

*Botanical.*—*Prunus dulcis.*

Parentage:

*Female, or seed parent.*—*Prunus dulcis* variety designated 'Le Grand', unpatented.

*Male, or pollen parent.*—Australian *Prunus dulcis* variety designated 'Keane', unpatented.

Propagation:

*Type.*—Budding onto rootstock.

*Time to initiate roots.*—NA.

*Time to produce young plant.*—Eight months.

*Root description.*—'Nemaguard' (unpatented) rootstock.

Plant description:

Tree:

*Size.*—Similar to Nonpareil. Mature tree height is approximately 4.5 meters with a spread of approximately 4 meters at 11 years of age.

*Vigor.*—Medium to strong.

*Density.*—Medium to high.

*Habit.*—Slightly open.

Trunk:

*Diameter.*—At 4 years of age, about 15 cm wide and about 54.2 cm high.

*Texture.*—Slightly rough.

*Color of bark.*—RHS 177A, moderate reddish brown.

*Lenticels length.*—About 5.2 mm.

*Lenticels width.*—About 1.4 mm.

*Lenticels density.*—About 4 per $cm^2$ on nine year-old wood.

*Lenticels shape.*—Narrow elliptic.

*Lenticels color.*—RHS 166D, moderate orange.

Current season shoot:

*Shape in cross section.*—Round.

*Color.*—RHS 141C, strong yellowish green.

*Texture.*—Smooth and glabrous.

One year-old shoot:

*Length.*—Up to about 90 cm.

*Texture.*—Smooth.

*Internode length.*—About 9-35 mm.

*Thickness.*—Medium, About 3-4.5 mm.

*Shape in cross section.*—Round.

*Color.*—RHS N197D, greyish yellow green.

*Anthocyanin coloration.*—Strong coloration on sunny side; Upper surface color: RHS 175A; Lower surface color: RHS 144A.

*Intensity of anthocyanin coloration.*—Medium to strong.

*Feathering.*—Slight.

*Lenticels.*—Present.

*Lenticels density.*—About 22-25 per $cm^2$.

*Lenticels shape.*—Elliptic.
*Lenticels length.*—About 2.3-3.9 mm.
*Lenticels width.*—About 1 mm.
*Lenticels color.*—RHS 22D.

Buds:
*Shape.*—Lateral: obtuse; Terminal: acute.
*Length.*—Lateral: About 4.5-4.7 mm; Terminal: About 4.5-5.5 mm.
*Diameter.*—Lateral: About 3.0-3.2 mm; Terminal: About 2.6-2.8 mm.
*Color.*—Lateral: RHS 200D; Terminal: RHS 200B.

Spurs:
*Shape.*—Cylindrical.
*Length.*—About 14.2-22.8 mm.
*Diameter.*—About 4.8-4.9 mm.
*Color.*—RHS 200C.
*Leaves per spur.*—About 9.55.

Mature wood:
*Color.*—RHS 177B.

Foliage:
*Density.*—Loose to medium.

Leaf blade:
*Length.*—About 45-58 mm, average 49.5 mm.
*Width.*—About 12-19 mm, average 15 mm.
*Length/width ratio.*—Low.
*Shape.*—Elliptic.
*Shape of base.*—Obtuse.
*Shape of apex.*—Acute.
*Color.*—Upper surface: RHS NN137B, greyish olive green.
*Incisions of margin.*—Crenate.
*Venation type.*—Arcuate to pinnate.

Petiole:
*Length.*—About 12-20 mm, average 15.5 mm.
*Color.*—RHS 144A, strong yellow green.
*Shape in cross section.*—Concave.

Flower buds:
*Distribution.*—Almost always on spurs.
*Shape.*—Conical.
*Color of tip of petals.*—RHS 62D, pale purplish pink.
*Color of sepals.*—RHS 185B, moderate red.
*Hairiness of sepals.*—Absent or very weak.

Flower:
*Diameter of flower.*—About 37-44.5 mm, average 40.7 mm, medium.
*Depth of flower.*—About 14.86 mm (average).
*Number of flowers.*—Single or clusters.
*Texture of flowers.*—Smooth.
*Scent of flowers.*—Strong fragrance.
*Length of petals.*—About 17.3 mm (average).
*Width of petals.*—About 11.26 mm (average).
*Texture of petals.*—Upper surface: Velvet; Lower surface: Velvet.
*Margin.*—Indented, retuse, two lobes.
*Shape of petals.*—Narrow elliptic to elliptic.
*Shape of apex.*—Retuse, indented.
*Shape of base.*—Acute.
*Number of petals.*—Five.
*Color of petals.*—Upper surface: RHS 69D; Lower surface: RHS 69D.
*Number of stamens.*—About 38.2 (average).
*Color of stamens.*—White.
*Number of pistils.*—Always one.
*Length of pistils.*—About 13.51 mm (average).
*Color of pistils.*—RHS 12D with white hairs on lower half.
*Position of stigma as compared with anthers.*—Below.

Sepals:
*Number.*—Five.
*Shape.*—Broad elliptic.
*Length.*—About 5.29 mm (average).
*Width.*—About 4.02 mm (average).
*Apex.*—Rounded.
*Margin.*—Medium hairiness.
*Color.*—Outer surface: RHS 138B with some anthocyanin 187C; Inner surface: RHS 138B with nectary 17A.

Pedicels:
*Length.*—About 2.19 mm (average).
*Color.*—RHS 144C.

Stamen:
*Anthocyanin coloration of filament.*—White.
*Length of filament.*—About 8.02 mm (average).

Stigma:
*Size.*—Small to medium.

Pollen:
*Amount.*—Abundant.
*Color.*—RHS 153D.

Green fruit:
*Size.*—Medium.
*Shape.*—Ovate.
*Average length.*—About 32.5 mm.
*Average width.*—About 25.64 mm.
*Average thickness.*—About 21.72 mm.
*Color.*—RHS 146C, moderate yellow green.
*Pubescence.*—Medium.

Dry fruit:
*Shape.*—Ovate.
*Shape of apex.*—Pointed.
*Length.*—About 26-33 mm.
*Width.*—About 17-21 mm.
*Thickness.*—About 13-16 mm.
*Average weight.*—About 1.9 g.
*Color.*—RHS 165B, brownish orange.
*Surface.*—Slightly rough with moderate pitting.
*Thickness of endocarp.*—About 1.5-2.5 mm.
*Resistance to cracking.*—Very low, papershell.
*Percentage of kernel to dry fruit.*—Approximately 58%.
*Keel development.*—Medium to strong.
*Distribution on tree.*—Mostly on spurs.
*Base.*—Obtuse.
*Color.*—Inner surface: RHS 164D.

Fruit:
*Percentage of double kernels.*—None.
*Eating quality.*—Excellent. Oil content average is about 54.7%; Oleic acid is about 67.5%, Vitamin E is about 48.6 mg/100 g oil.
*Production.*—Regular fruit bearer.

Kernel:
*Shape.*—Elliptic.
*Size.*—Medium.
*Average weight.*—About 1.18 g.
*Length.*—About 19-24 mm.
*Width.*—About 11-13 mm.
*Thickness.*—About 8-9 mm.
*Main color.*—RHS 164B, moderate orange yellow.
*Intensity of color.*—Light.
*Rugosity.*—Weak to medium.

*Taste.*—Slight semibitter.

*Apex.*—Acute.

*Base.*—Acute.

*Yield.*—About 4,633 kg/ha at 10 years of age.

Blooming/flowering timing:

*Time of beginning of flowering.*—Early to late August (winter — Australia); Full bloom four to six days before 'Nonpareil'.

*Time of leaf budburst in relation to beginning of flowering.*—Well after flowering has almost ended.

*Flowering period.*—Early to late August (winter — Australia); Approximately three and one half weeks depending on the weather; Full bloom about mid-August.

*Pollen compatibility.*—Self-incompatible, compatible with 'Nonpareil'. (unpatented), 'Monterey' (unpatented), 'Sonora' (unpatented), and 'Peerless' (unpatented).

*Time of maturity.*—Approximately 32 weeks from beginning of flowering (about 7.5 months from August to March/April — Australia).

Cultural characteristics:

*Susceptibility to disease.*—Very good tolerance to bacterial spot.

Storage/shipping:

*Storage.*—Good storage ability due to high level of oleic acid (about 62%).

*Shipping ability.*—Good.

Harvest:

*Peak.*—March (early Autumn — Australia); Approximately 22 days after Nonpariel.

Pest resistance/susceptibility:

*Resistance.*—Well sealed paper shell is resistant to insect attacks.

We claim:

1. A new and distinct variety of almond tree (*Prunus dulcis*) named 'RHEA', as illustrated and described herein.

* * * * *